United States Patent [19]

Cody et al.

[11] Patent Number: 5,786,335
[45] Date of Patent: Jul. 28, 1998

[54] SULFHYDRYL CONTAINING PEPTIDES FOR TREATING VASCULAR DISEASE

[75] Inventors: Wayne Livingston Cody, Saline; Helen Tsenwhei Lee; Randy Ranjee Ramharack, both of Ann Arbor; Bruce David Roth, Plymouth; Tomi Sawyer, Ann Arbor; Drago Robert Sliskovic, Saline, all of Mich.

[73] Assignee: Warner-Lambert Company, Morris Plains, N.J.

[21] Appl. No.: 744,698

[22] Filed: Oct. 31, 1996

Related U.S. Application Data

[60] Provisional application No. 60/007,250, Nov. 16, 1995.
[51] Int. Cl.$^6$ .............................. C07K 5/00; C07K 7/00; C07K 16/00; A61K 38/00
[52] U.S. Cl. ................................. 514/17; 514/16; 514/18; 530/379; 530/330; 530/331
[58] Field of Search .............................. 514/2, 17, 18, 514/16; 530/329, 330, 331

[56] References Cited

U.S. PATENT DOCUMENTS

| | | |
|---|---|---|
| 4,256,632 | 3/1981 | Levin et al. . |
| 5,223,409 | 6/1993 | Ladner et al. .................. 435/69.7 |
| 5,382,569 | 1/1995 | Cody et al. ..................... 514/17 |
| 5,428,019 | 6/1995 | Edwards et al. ................. 514/16 |

FOREIGN PATENT DOCUMENTS

| | | |
|---|---|---|
| 519547A | 12/1992 | European Pat. Off. . |
| 9102001 | 2/1991 | WIPO . |
| 9313206 | 7/1993 | WIPO . |
| 9318141 | 9/1993 | WIPO . |

OTHER PUBLICATIONS

Gregouàdis, C. et al. 1993. Trends in Biotech 11:440–442.
Wozniak, R. W. et al. 1994. J. all Biol. 125 : 31–42.
Kiel, JA. et al. 1992. DNA Seg. 3 : 221–232.
Rodriguez, R. et al. 1985. Biochem. Int. 11: 841–843.
Herman, S. et al. 1993. Bioconjugated 4(5): 402–405.
Bostom. et al., *JAMA*, vol. 276, No. 7, pp. 544–548 (1996).
Trieu, et al. *Biochem Journal*, vol. 307, pp. 17–22 (1995).
Guevara, Jr., et al. *Biophysical Journal*, vol. 64, pp. 686–700 (1993).

*Primary Examiner*—Sheela Huff
*Attorney, Agent, or Firm*—Charles W. Ashbrook

[57] ABSTRACT

Sulfhydryl containing peptides having the formula

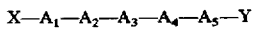

$$X-A_1-A_2-A_3-A_4-A_5-Y$$

inhibit the formation of Lp(a) and thus are useful for treating vascular diseases such as coronary heart disease, myocardial infarction, ischemic stroke, cervical atherosclerosis, cerebral infarction, and restenosis.

8 Claims, No Drawings

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ile Gln Cys Tyr Lys
1               5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala Gln Cys Tyr Lys
1               5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ile Gln Cys Tyr Lys
1               5
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3
        ( D ) OTHER INFORMATION: /note="Cys is N-methylated"

( x i ) SEQUENCE DESCRIPTION: SEQ ID NO:4:

```
Ile Gln Cys Tyr Lys
1               5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Ile Gln Cys Ala Lys
1               5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single ( D ) TOPOLOGY: linear ( i i ) MOLECULE TYPE: peptide ( i x ) FEATURE:
    ( A ) NAME/KEY: Peptide
    ( B ) LOCATION: 5
    ( D ) OTHER INFORMATION: /note="Lys is Lys-NH2"

( x i ) SEQUENCE DESCRIPTION: SEQ ID NO:6:

```
Ala  Gln  Cys  Tyr  Lys
 1                    5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="Ile is Ac-Ile"

( x i ) SEQUENCE DESCRIPTION: SEQ ID NO:7:

```
Ile  Gln  Cys  Ala  Lys
 1                    5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="Ala is Ac-Ala"

( i x ) FEATURE:
        ( A ) NAME/KEY: Peptide
        ( B ) LOCATION: 5
        ( D ) OTHER INFORMATION: /note="Lys is Lys-NH2"

( x i ) SEQUENCE DESCRIPTION: SEQ ID NO:8:

```
Ala  Gln  Cys  Tyr  Lys
 1                    5
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 5
        ( D ) OTHER INFORMATION: /note="Cys is N-methylated"

( x i ) SEQUENCE DESCRIPTION: SEQ ID NO:9:

```
Ala  Gln  Cys  Tyr  Cys
```

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Gln Cys Tyr Lys
    1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 4
        ( D ) OTHER INFORMATION: /note="Lys is Lys-NH2"

( x i ) SEQUENCE DESCRIPTION: SEQ ID NO:11:

Gln Cys Tyr Lys
    1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Ala Cys Tyr Lys
    1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Gln Cys Ala Lys
    1

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
                ( A ) NAME/KEY: Peptide
                ( B ) LOCATION: 1
                ( D ) OTHER INFORMATION: /note="Ala is N-methylated"

( x i ) SEQUENCE DESCRIPTION: SEQ ID NO:14:

Ala  Cys  Tyr  Lys
        1

( 2 ) INFORMATION FOR SEQ ID NO:15:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 2
                ( D ) OTHER INFORMATION: /note="Cys is N-methylated"

( x i ) SEQUENCE DESCRIPTION: SEQ ID NO:15:

Gln  Cys  Tyr  Lys
        1

( 2 ) INFORMATION FOR SEQ ID NO:16:

( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Peptide
                ( B ) LOCATION: 3
                ( D ) OTHER INFORMATION: /note="Tyr is N-tert-butylated"

( x i ) SEQUENCE DESCRIPTION: SEQ ID NO:16:

Gln  Xaa  Tyr  Lys
        1

SULFHYDRYL CONTAINING PEPTIDES FOR TREATING VASCULAR DISEASE

This application claims the benefit of U.S. Provisional Application No. 60/007,250 filed Nov. 6, 1995.

FIELD OF THE INVENTION

This invention provides sulfhydryl containing tripeptides, tetrapeptides, and pentapeptides that inhibit the formation of lipoprotein(a), and are thus useful for treating vascular disease.

BACKGROUND OF THE INVENTION

Lipoprotein(a), or "Lp(a)," is a macromolecule present in human plasma. While the physiological function of Lp(a) is unknown, elevated plasma levels have been associated with a variety of vascular diseases, including coronary heart disease, myocardial infarction, ischemic stroke, cervical atherosclerosis, cerebral infarction, and even restenosis following percutaneous transluminal coronary angioplasty. One method to treat such vascular diseases is thus to lower plasma concentrations of Lp(a).

The Lp(a) macromolecule is a complex comprised of low-density lipoproteins (LDL) and a hydrophilic glycoprotein known as apolipoprotein (a), or "apo(a)." The major component of LDL is a protein known as apolipoprotein B-100, or "apo B-100." Both apo B-100 and apo(a) have unpaired cysteine residues as part of their backbone. These unpaired cysteine residues come together to form a disulfide bond, thus coupling apo B-100 together with apo(a) to produce Lp(a). One method for reducing plasma levels of Lp(a) is to inhibit its formation; for instance, by inhibiting the coupling of apo B-100 to apo(a).

We have now discovered certain tripeptides, tetrapeptides, and pentapeptides which are effective at inhibiting Lp(a) formation. The compounds are thus useful for treating vascular diseases characterized by elevated plasma levels of Lp(a).

SUMMARY OF THE INVENTION

This invention provides tripeptides, tetrapeptides, and pentapeptides useful for treating vascular diseases characterized by elevated plasma concentrations of Lp(a). The invention further provides a method for treating vascular diseases and for inhibiting Lp(a) formation comprising administering a tripeptide, tetrapeptide, or pentapeptide.

More particularly, this invention provides peptides of Formula I $$X-A_1-A_2-A_3-A_4-A_5-Y \qquad I$$

wherein:

X is an amino terminal substituent selected from hydrogen, 1 or 2 alkyl groups from 1 to 16 carbon atoms, an acyl group from 2 to 16 carbon atoms, carbobenzyloxy, or t-butyloxycarbonyl;

$A_1$ is Ile, Ala, or a bond;

$A_2$ is Gln, Ala, or a bond;

$A_3$ is Cys or substituted Cys of the formula

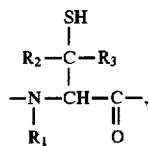

where $R_1$, $R_2$, and $R_3$ independently are hydrogen or $C_1$–$C_4$ alkyl;

$A_4$ is Tyr or Ala;

$A_5$ is Lys; and

Y is a carboxy-terminal substituent, bonded to the carbonyl group of the $A_5$ amino acid, selected from OH, $C_1$–$C_8$ alkoxy, $NH_2$, $C_1$–$C_8$ alkyl NH—, di-($C_1$–$C_8$) alkyl N—, or a pharmaceutically acceptable salt thereof.

A preferred embodiment are pentapeptides, i.e., compounds of Formula I wherein $A_1$ is Ile or Ala, and $A_2$ is Gln or Ala. Especially preferred pentapeptides are the following:

Ile—Gln—Cys—Tyr—Lys (SEQ ID NO: 1);
Ala—Gln—Cys—Tyr—Lys (SEQ ID NO: 2);
Ile—Ala—Cys—Tyr—Lys (SEQ ID NO: 3);

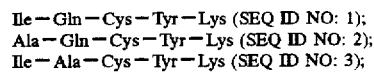
Ile—Gln—N—CH—C—Tyr—Lys (SEQ ID NO: 4);
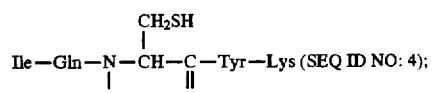
Ile—Gln—Cys—Ala—Lys (SEQ ID NO: 5);
Ala—Gln—Cys—Tyr—Lys—$NH_2$ (SEQ ID NO: 6);
Ac—Ile—Gln—Cys—Ala—Lys (SEQ ID NO: 7);
Ac—Ala—Gln—Cys—Tyr—Lys—$NH_2$ (SEQ ID NO: 8); or
Ala—Gln—(N—$CH_3$)Cys—Tyr—Lys (SEQ ID NO: 9).

Another preferred embodiment are tripeptides of Formula I, i.e., where $A_1$ and $A_2$ both are a bond. Especially preferred tripeptides are:

Cys—Tyr—Lys;
Cys—Ala—Lys;
Cys—Ala—Lys—$NH_2$;
Ac—Cys—Tyr—Lys—$NH_2$;
(N—$CH_3$)Cys—Tyr—Lys; or

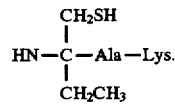
HN—C—Ala—Lys.
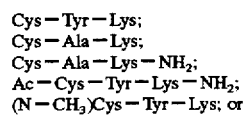

Also preferred are tetrapeptides of Formula I, i.e., wherein one of $A_1$ or $A_2$ is a bond. Especially preferred tetrapeptides include:

Gln—Cys—Tyr—Lys (SEQ ID NO: 10);
Gln—Cys—Tyr—Lys—$NH_2$ (SEQ ID NO: 11);
Ala—Cys—Tyr—Lys (SEQ ID NO: 12);
Gln—Cys—Ala—Lys (SEQ ID NO: 13);
(N—$CH_3$)Ala—Cys—Tyr—Lys (SEQ ID NO: 14);
Gln—(N—$CH_3$)Cys—Tyr—Lys (SEQ ID NO: 15); and

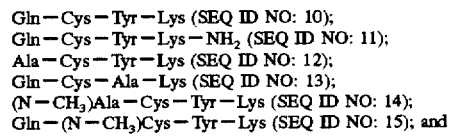
Gln—NH—CH—CO—(N-tBu)Tyr—Lys (SEQ ID NO: 16).
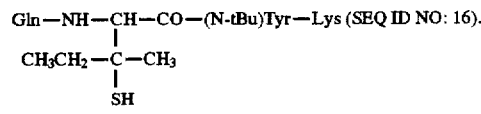

Another embodiment of this invention is a pharmaceutical formulation comprising a peptide of Formula I together with a pharmaceutically acceptable excipient, diluent, or carrier.

Also provided is a method for treating vascular disease in an animal suffering therefrom comprising administering an Lp(a) lowering amount of a compound of Formula I. The

3 invention also provides a method of inhibiting Lp(a) formation in an animal comprising administering an Lp(a) inhibiting amount of a compound of Formula I to an animal in need thereof.

DETAILED DESCRIPTION OF THE INVENTION

In the above formula, $A_1$ can include Ile and Ala. These are common abbreviations for the amino acids isoleucine and alanine, respectively. As used herein, all amino acids referred to by abbreviations include both the individual L-isomer and the D-isomer. Preferred peptides are those made with L-amino acids. $A_2$ in the above formula includes Gln, which designates glutamine. The term "Cys" means cysteine, and "Tyr" means tyrosine. Any of the amino acids making up the peptides of the invention can be N-alkylated, for instance with a $C_1$-$C_4$ alkyl group. "$C_1$-$C_4$ alkyl" means straight and branched aliphatic radicals, such as methyl, ethyl, isopropyl, n-butyl, tert.-butyl, and the like. Typical N-alkylated amino acids include (N—$CH_3$)Tyr, (N—$CH_2CH_3$)Cys, (N-tertBu)Ala, and the like.

The structures of the peptides of Formula I are written in customary form, namely with the amino terminal end at the left side of the page, and the carboxy terminal end at the right side of the page.

As noted above, "X" defines an amino terminal substituent selected from hydrogen, 1 or 2 $C_1$-$C_{16}$ alkyl groups, a $C_2$-$C_{16}$ carbon acyl group, carbobenzyloxy, or t-butyloxycarbonyl. The term "$C_1$-$C_{16}$ alkyl" refers to straight, branched, and cyclic hydrocarbon chains having up to 16 carbon atoms. Typical examples of $C_1$-$C_{16}$ alkyl groups include methyl, ethyl, n-propyl, isopropyl, n-butyl, tert.-butyl, isopentyl, 1,1-dimethylheptyl, cyclopropyl, cyclohexyl, cyclopentylmethyl, octyl, and 1,2,3-triethyldecyl.

Acyl groups having $C_2$-$C_{16}$ carbon atoms are straight, branched, cyclic, saturated, and unsaturated acyl groups having 1 or 2 carbonyl moieties per group. Typical examples include acetyl, benzoyl, succinoyl, cinnamoyl, 3,4-dihydroxycinnamoyl, palmityl, lauryl, octanoyl, and glutaryl. Both alkyl and acyl substituents are taken to include those groups with halogen substituents, where a halogen group is, for example, fluoro, chloro, bromo, or iodo. A typical haloacyl group thus is trifluoroacetyl, and a typical haloalkyl group is 2,2,2,-trichloroethyl.

The term "Y" in Formula I designates the chemical group(s) that may be utilized to substitute or modify the terminal carboxy group of the peptide. Y may thus be a terminal carboxy acid (—OH), a $C_1$-$C_8$ alkoxy ester forming group such as methoxy, ethoxy, tert.-butoxy, octyloxy, and the like, as well as a carboxamide forming group (—$NH_2$). The carboxamide group may be substituted by 1 or 2 $C_1$-$C_8$ alkyl moieties, such as, for example, methylamide, N,N-dimethylamide, N-ethyl-N-isohexylamide, and the like.

The peptides of Formula I can form pharmaceutically acceptable salts when Y is OH (to form a terminal carboxy group) or when X is hydrogen, or 1 or 2 alkyl groups (to form a terminal amino, alkylamino, or dialkylamino group). Reaction of the peptides having a terminal amino group with an organic or inorganic acid produces the pharmaceutically acceptable salt. Typical acids commonly employed include mineral acids such as hydrochloric acid, phosphoric acid, sulfonic acid, and the like. Organic acids which can be employed include oxalic acid, malonic acid, tartaric acid, succinic acid, citric acid, and the like. Salts of the terminal carboxylic acid moiety (i.e., Y is OH) are formed by reacting the peptide with common organic or inorganic bases, examples of which include amines such as methylamine, triethylamine, procaine, benzylamine, piperidine, as well as inorganic bases such as sodium hydroxide, potassium hydroxide, calcium carbonate, magnesium hydroxide, and the like.

The tri-, tetra-, and pentapeptides of this invention are readily prepared utilizing common methodology. For example, the compounds of Formula I can be prepared by solid-phase peptide synthesis employing a commercially available peptide synthesizer, for example, a 431A Peptide Synthesizer available from Applied Biosystems. The synthesizer utilizes standard solid-phase peptide techniques, for example, by utilizing N-alpha-Fmoc (9-fluorenylmethyloxycarbonyl) protected amino acids on a p-alkoxybenzyl alcohol resin (e.g., Wang resin to give peptides where Y is OH, a Rink resin to give peptides where Y is $NH_2$). Most of the peptides were prepared on a 0.25 mmol scale using a common peptide coupling reagent. Typical coupling reagents include DCC (dicyclohexylcarbodiimide) and EEDQ (2-ethoxy-1-ethoxycarbonyl-1,2-dihydroquinoline). The coupling can also be conducted using an anhydride or an active ester formed with a reagent such as HOBt (N-hydroxybenzotriazole). In a preferred process, the amino acids are single coupled as either their symmetrical anhydrides or as HOBt-activated esters. The progress of the coupling reaction is monitored by the Kaiser ninhydrin test. If incomplete incorporation of the acylating agent is indicated, the amino acid is recoupled until a negative Kaiser ninhydrin test is obtained. Following each coupling reaction, the protecting groups are removed by standard methods, for instance, in the case of N-alpha-Fmoc, by stirring the peptide in 20% v/v piperidine in N-methyl-pyrrolidinone prior to incorporation of the next N-protected amino acid.

N-acylpeptides are prepared, following coupling of the last amino acid, by deblocking the N-alpha amino group, and reacting the deprotected peptide with an equivalent amount or slight excess of an acylating agent such as 1-acetylimidazole or acetic anhydride in a mutual organic solvent such as dichloromethane or tetrahydrofuran. An acid scavenger such as triethylamine or 4-(dimethylamino) pyridine can be utilized, if desired.

The peptide-resin upon which all couplings and N-terminal modifications have been completed is then washed with dimethylformamide and dichloromethane and dried in a vacuum. The peptide is readily cleaved from the resin by stirring the resin with a strong acid, for instance 95% v/v trifluoroacetic (TFA) acid/water, or with a standard solution such as Reagent K (82.5% trifluoroacetic acid, 5% phenol, 5% water, 5% thioanisol, and 2.5% ethanedithiol). The cleavage generally is substantially complete after about 2 to 4 hours when carried out at a temperature of about 20° C. to about 40° C. The resin is separated from the peptide by filtration, and the solvents are removed from the filtrate by evaporation under reduced pressure. The peptide is further purified, if desired, by conventional techniques, for instance by reversed-phase high-performance liquid chromatography utilizing a support such as a C18 column (e.g., Vydac 218TP1022, 2.2×25.0 cm, 15.0 mL/min). A typical solvent routinely utilized to elute the peptide is a linear gradient such as 0.1% v/v TFA in water or 0.1% v/v TFA in acetonitrile. The homogeneity and composition of the resulting peptide is established by routine methods, for instance by analytical reversed-phase high-performance liquid chromatography (e.g., utilizing a Vydac 218TP54, 0.46×25 cm column) or a C18 column, employing a linear gradient such as those described above. Other analytical techniques can be employed, such as capillary electrophoresis, thin-layer chromatography, proton nuclear magnetic resonance spectrometry, and fast atom bombardment or electrospray mass spectrometry. Routine amino acid analysis can also be employed to characterize the peptides.

The tri-, tetra-, and pentapeptides of the invention can be formulated by conventional methods for both oral and parenteral administration to animals for treating vascular diseases and inhibiting formation of Lp(a). The compounds can be administered by injection, including intravenously, intramuscularly, subcutaneously, and intraperitoneally. The compounds can also be formulated for transdermal delivery, intranasal delivery, and as suppositories.

The formulations of the invention will typically contain from about 5% to about 95% by weight of peptide together with one or more pharmaceutically acceptable carriers, diluents, excipients, binders, flavoring agents, and the like. The formulations can be in solid or liquid form, typical solids being tablets, capsules, dispersible granules, lyophilized powders which can be dissolved in isotonic saline, 5% aqueous glucose, sterile water, or the like.

Typical excipients and diluents commonly employed include magnesium carbonate, talc, sugar, dextrin, starch, gelatin, methylcellulose, cocoa butter, and the like. Transdermal preparations generally will employ polymers, low-melting waxes, penetration enhancing agents, and the like. The peptides can be mixed with common inhalants for intranasal administration.

Liquid preparations can be in the form of solutions, suspensions, emulsions, and the like, for instance when mixed with water or water-containing propylene glycol, dextrose, sodium chloride, and the like. A preferred method for administering the peptides is by parenteral injection, for instance as an aqueous polyethylene glycol solution.

The compounds are also amenable to oral delivery as an aqueous solution or syrup. Such preparations may include suitable coloring agents, flavoring agents, stabilizing agents, and the like. The tri- and pentapeptides will be administered to an animal, including a human, in an amount that is effective to inhibit Lp(a) formation. Such "effective amount" will generally be from about 0.1 to about 100 mg/kg of animal body weight, and more normally from about 1.0 to about 50 mg/kg. Such doses can be administered from 1 to about 4 times a day. The exact dosage regimen will, of course, depend upon the severity of the vascular disease being treated, as well as the potency of the particular peptide being utilized. Such preferred dosage regimens will generally be determined by an attending medical practitioner.

The following examples further illustrate the synthesis and characterization of representative peptides of Formula I.

EXAMPLE 1

Cys-Tyr-Lys-NH$_2$

The linear peptide is prepared by standard solid-phase synthetic peptide methodology utilizing a Fmoc/t-butyl strategy (Fields G. B. and Noble R. L., *Int. J. Peptide Protein Res.*, 1990;35:161–214). All protected amino acids and reagents are obtained from commercial sources and not further purified. The protected peptide resin is prepared in a shaker, utilizing protocols supplied for a diisopropylcarbodiimide mediated coupling scheme. Starting with 1.67 g of Rink resin (0.60 meq/g, 1 meq of resin total), the protected peptide is prepared by the stepwise coupling of the following protected amino acids (in order of addition): N-epsilon-Boc-N-alpha-Fmoc-1-Lys, N-Fmoc-t-butyl-1-Tyr, and N-Fmoc-s-Trityl-1-Cys. A typical cycle for the coupling of an individual amino acid residue is illustrated below.

All single coupling reaction vessel cycles conform to the following pattern:

1. Two 10 minute washes with N,N-Dimethyl-formamide (DMF)
2. 20% Piperidine in DMF for 5 minutes
3. 20% Piperidine in DMF for 20 minutes
4. Three washes with DMF
5. Coupling Period:

The coupling period consists of a 2 hour cycle in which the protected amino acid, 0.408 g HOBt (135.1 g/mol, 3 meq), and 0.48 mL diisopropylcarbodiimide (DIC) (126.2 g/mol, 3 meq) are shaken with the deprotected peptide resin.
6. Three washes with DMF
7. Ninhydrin test*
8. Back to Step 2

* If ninhydrin test gives a positive result, another coupling period cycle is performed for 1 hour, using 1 meq of the protected amino acid, HOBt, and DIC.

After addition of N-Fmoc-s-Trityl-1-Cys, the tripeptide was washed 3 times with dichloromethane (DCM) and dried under reduced pressure.

The peptide is liberated from the solid resin support and completely deprotected by treatment with 95% TFA, 2.5% water, and 2.5% 1,2-ethanedithiol for 2 hours at room temperature. After filtration, the TFA is removed under reduced pressure, and the crude peptide is precipitated from diethyl ether, filtered, solubilized in aqueous solution (70% CH$_3$CN/30% H$_2$O), and lyophilized. The crude peptide is purified by reversed-phase high-performance liquid chromatography (RP-HPLC) using a C18 column (Vydac 218TP1022) with a linear gradient of 0–50% B over 120 minutes (A=0.01% TFA/H$_2$O; B=0.01% TFA/CH$_3$CN). Individual fractions are collected and combined based upon analysis by analytical HPLC. The combined fractions are then lyophilized. The homogeneity and structure of the resulting peptide is confirmed by analytical HPLC, electrospray mass spectrometry (ES-MS), and amino acid analysis. M$^+$412.6.

EXAMPLE 2

Ile-Gln-Cys-Tyr-Lys (SEQ ID No: 1)

The linear peptide is prepared by standard solid-phase synthetic peptide methodology utilizing a Fmoc/t-butyl strategy (Fields G. B. and Noble R. L., *Int. J. Peptide Protein Res.*, 1990;35:161–214). All protected amino acids and reagents are obtained from commercial sources and not further purified. The protected peptide resin is prepared on an Applied Biosystems 431A Peptide Synthesizer, utilizing protocols supplied for a dicyclohexylcarbodiimide mediated coupling scheme (Version 2.0 Fmoc). Starting with 0.39 g of N-α-Fmoc-Lys(Boc)-Wang resin (0.65 meq/g, resin substitution, 0.25 meq of N-α-Fmoc-Lys(Boc) total), the protected peptide is prepared by the stepwise coupling of the following protected amino acids (in order of addition): 1.0 meq of N-α-Fmoc-Tyr(tBu), 1.0 meq of N-α-Fmoc-Cys (Trt), 1.0 meq of N-α-Fmoc-Gln, and 1.0 meq of N-α-Fmoc-Ile. A typical cycle for the coupling of an individual amino acid residue is illustrated below (reproduced from the ABI 431A manual, Version 1.12).

All single coupling reaction vessel cycles conform to the following pattern:

1. One wash with N-methylpyrrolidone (NMP).

2. 20% piperidine in NMP for 3 minutes.

3. 20% piperidine in NMP for 15 minutes.

4. One wash with NMP.

5. Eight washes with dichloromethane (DCM).

6. Six washes with NMP.

7. Coupling period.

After coupling of N-α-Fmoc-Ile, the Fmoc group is removed by treatment with 20% piperidine in NMP as above, washed with DCM, and dried under reduced pressure.

The peptide is liberated from the solid support and completely deprotected by treatment with 82.5% TFA, 5.0% phenol, 5.0% water, 5.0% thioanisole, and 2.5% 1,2-ethanedithiol for 2 hours at room temperature. After filtration, the TFA is removed under reduced pressure, and the crude peptide is precipitated from diethyl ether, filtered, solubilized in aqueous solution, and lyophilized (100 mg). The crude peptide is purified by reversed phase-high performance liquid chromatography (RP-HPLC) using a C18 column (Vydac 218TP1022) with a linear gradient of 0–50% B over 120 minutes (A=0.1% TFA/$H_2O$; B=0.1% TFA/$CH_3CN$). Individual fractions are collected and combined based upon analysis by analytical HPLC. The combined fractions are concentrated under reduced pressure (10 mL), diluted with water (50 mL), and lyophilized (20 mg). The homogeneity and structure of the resulting peptide is confirmed by analytical HPLC, proton nuclear magnetic resonance spectroscopy ($H^1$-NMR), and fast atom bombardment mass spectrometry (FAB-MS), $MH^+$653.9.

EXAMPLE 3

Ac-Cys-Tyr-Lys

The linear peptide is prepared by standard solid-phase synthetic peptide methodology utilizing a Fmoc/t-butyl strategy (Fields G. B. and Noble R. L., *Int. J. Peptide Protein Res.*, 1990;35:161–214). All protected amino acids and reagents are obtained from commercial sources and not further purified. The protected peptide resin is prepared in a shaker, utilizing protocols supplied for a diisopropylcarbodiimide mediated coupling scheme. Starting with 1.54 g of N-epsilon-Boc-N-alpha-Fmoc-1-Lys resin (0.65 meq/g, 1 meq of resin total), the protected peptide is prepared by the stepwise coupling of the following protected amino acids (in order of addition): N-Fmoc-t-butyl-1-Tyr and N-Fmoc-s-Trityl-1-Cys. A typical cycle for the coupling of an individual amino acid is illustrated below.

All single coupling reaction vessel cycles conform to the following pattern:

1. Two 10 minute washes with N,N-Dimethyl-formamide (DMF)

2. 20% Piperidine in DMF for 5 minutes 3. 20% Piperidine in DMF for 20 minutes

4. Three washes with DMF

5. Coupling Period:

The coupling period consists of a 2 hour cycle in which the protected amino acid, 0.408 g HOBt (135.1 g/mol, 3 meq), and 0.48 mL diisopropylcarbodiimide (DIC) (126.2 g/mol, 3 meq) are shaken with the deprotected peptide resin.

6. Three washes with DMF

7. Ninhydrin test*

8. Back to Step 2

* If ninhydrin test gives a positive result, another coupling period cycle is performed for 1 hour, using 1 meq of the protected amino acid, HOBt, and DIC.

The tripeptide is capped with the acetyl group using the following procedure:

1. 20% Piperidine in DMF for 5 minutes 2. 20% Piperidine in DMF for 20 minutes

3. Two shakes with 50% acetic anhydride in DMF for 1 hour

4. Three washes with DMF

5. Ninhydrin test

6. If ninhydrin test is positive, repeat cycle starting from Step 3, as necessary.

After capping of the tripeptide, the tripeptide was washed 3 times with dichloromethane (DCM) and dried under reduced pressure.

The peptide is liberated from the solid resin support and completely deprotected by treatment with 95% TFA, 2.5% water, and 2.5% 1,2-ethanedithiol for 2 hours at room temperature. After filtration, the TFA is removed under reduced pressure, and the crude peptide is precipitated from diethyl ether, filtered, solubilized in aqueous solution (70% $CH_3CN$/30% $H_2O$), and lyophilized. The crude peptide is purified by reversed-phase high-performance liquid chromatography (RP-HPLC) using a C18 column (Vydac 218TP1022) with a linear gradient of 0–50% B over 120 minutes (A=0.01% TFA/$H_2O$; B=0.01% TFA/$CH_3CN$). Individual fractions are collected and combined based upon analysis by analytical HPLC. The combined fractions are then lyophilized. The homogeneity and structure of the resulting peptide is confirmed by analytical HPLC, ES-MS, and amino acid analysis, $M^+$455.5.

EXAMPLES 4–13

The following peptides were prepared by the general procedures described in Examples 1–3:

| | | |
|---|---|---|
| Lys—Cys—Lys | $MH^+$ | 377.5 |
| Ac—Cys—Tyr—Lys—$NH_2$ | $MH^+$ | 454.6 |
| Ala—Tyr—Lys | $MH^+$ | 380.5 |
| Cys—Ala—Lys | $MH^+$ | 320.5 |
| Cys—Tyr—Lys | $MH^+$ | 412.5 |
| Ala—Gln—Cys—Tyr—Lys (SEQ ID NO:2) | $MH^+$ | 611.71 |
| Ile—Ala—Cys—Tyr—Lys (SEQ ID NO:3) | $MH^+$ | 596.7 |
| Ile—Gln—Cys—Ala—Lys (SEQ ID NO:5) | $MH^+$ | 561.7 |
| Gln—Cys—Tyr—Lys—$NH_2$ (SEQ ID NO:11) | | |
| Cys—(N—$CH_3$)Tyr—Lys—$NH_2$ | | |

EXAMPLE 14

| Formulation for IV Administration | |
|---|---|
| Ingredient | Amount |
| Cys—Tyr—Lys Hydrochloride | 225 mg |
| Isotonic Saline | 450 mL |
| 10% Aqueous Glucose | 450 mL |

The above ingredients are mixed to form a solution capable of being infused into a subject suffering from myocardial infarction.

EXAMPLE 15

| Oral Formulation | |
|---|---|
| Cys—Tyr—Lys—NH$_2$ | 300 mg |
| Starch | 250 mg |
| Talc | 225 mg |

The above ingredients are blended to uniformity, and the mixture is pressed into a tablet for oral administration to a subject suffering from coronary heart disease and in need of treatment.

EXAMPLE 16

| Formulation for Injection | |
|---|---|
| Ile—Gln—Cys—Tyr—Lys (SEQ ID NO:1) Hydrochloride | 300 mg |

The peptide is dissolved in 50 mL of water and lyophilized to a white powder. The powder is placed in a vial for subsequent reconstitution by addition of sterile water. The resulting solution is well-suited to intramuscular injection for prevention of restenosis in a patient who has undergone a percutaneous transluminal coronary angioplasty.

As pointed out above, the peptides of this invention are useful for treating vascular diseases due to their ability to inhibit formation of Lp(a). The compounds have been evaluated in an in vitro assay which established that the subject compounds are potent inhibitors of Lp(a) formation. The assay was carried out by mixing approximately equal quantities of recombinant human apo(a) with low-density lipoprotein (LDL) in a 0.5 μL microcentrifuge tube. Control vessels contained no invention peptide, whereas test vessels contained a peptide of Formula I. The mixtures were incubated at 37° C. for 30 minutes. The coupling between apo(a) and LDL was quenched by addition of sodium dodecylsulfate (SDS)-PAGE loading buffer. The mixture is next resolved on 4% polyacrylamide gels, and Lp(a) is detected by western blotting using a monospecific human Lp(a) antibody. The intensity of the Lp(a) bands on the blots is measured by a commercial densitometer.

Table I below gives the percent inhibition of Lp(a) formation at 125 μM concentration of representative peptides of the invention, as well as the concentration of representative compounds required to inhibit 50% of Lp(a) formation (IC$_{50}$).

TABLE I

| | Lp(a) | |
|---|---|---|
| Compound Tested | % Inhibition at 125 μM | IC$_{50}$ |
| Ile—Gln—Cys—Tyr—Lys (SEQ ID NO:1) | 50.1 | 109 μM |
| Ala—Gln—Cys—Tyr—Lys (SEQ ID NO:2) | 36.9 | |
| Ile—Ala—Cys—Tyr—Lys (SEQ ID NO:3) | 29.8 | |
| Ile—Gln—Cys—Ala—Lys (SEQ ID NO:5) | 76.4 | |
| Cys—Tyr—Lys | 90.0 | 50 μM |

Additional compounds were evaluated in the above assay, and the western blots were visually inspected for changes in Lp(a) particle formation as a consequence of peptide mediated inhibition. Experimental lanes were visually compared to control lanes and assessed as follows: An easily detectable change from control was assigned as (+); a marked change from control was assigned as (++). Table II shows the results of several compounds of Formula I, in relative activity.

TABLE II

| | Relative Activity |
|---|---|
| Cys—Tyr—Lys | + (IC$_{50}$ = 50 μM) |
| Ac—Cys—Tyr—Lys—NH$_2$ | + |
| Cys—Tyr—Lys—NH$_2$ | ++ |

We claim:

1. A compound having the Formula I $$X-A_1-A_2-A_3-A_4-A_5-Y$$

wherein:

X is an amino terminal substituent selected from hydrogen, 1 or 2 alkyl groups from 1 to 16 carbon atoms, an acyl group from 2 to 16 carbon atoms, carbobenzyloxy, or t-butyloxycarbonyl;

$A_1$ is Ile, Ala, or a bond;

$A_2$ is Gln, Ala, or a bond;

$A_3$ is Cys or substituted Cys of the formula $$\begin{array}{c} SH \\ | \\ R_2-C-R_3 \\ | \\ -N-CH-C-, \\ | \quad \quad \| \\ R_1 \quad \quad O \end{array}$$

where $R_1$, $R_2$, and $R_3$ independently are hydrogen or $C_1-C_4$ alkyl;

$A_4$ is Tyr (N-tBu)Tyr or Ala;

$A_5$ is Lys; and

Y is a carboxy-terminal substituent, bonded to the carbonyl group of the $A_5$ amino acid, selected from OH, $C_1-C_8$ alkoxy, $NH_2$, $C_1-C_8$ alkyl NH—, di-($C_1-C_8$) alkyl N—, or a pharmaceutically acceptable salt thereof, with the proviso that X is not an acetyl group when $A_1$ and $A_2$ are a bond, $A_3$ is Cys, $A_4$ is Ala and Y is OH.

2. A compound of claim 1 wherein $A_1$ is Ile or Ala, and $A_2$ is Gln or Ala.

3. A compound of claim 2 which is

Ile-Gln-Cys-Tyr-Lys (SEQ ID NO: 1);

Ala-Gln-Cys-Tyr-Lys (SEQ ID NO: 2);

Ile-Ala-Cys-Tyr-Lys (SEQ ID NO: 3);

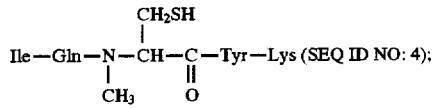

Ile-Gln-Cys-Ala-Lys (SEQ ID NO: 5);

Ala-Gln-Cys-Tyr-Lys-NH$_2$ (SEQ ID NO: 6);

Ac-Ile-Gln-Cys-Ala-Lys (SEQ ID NO: 7);

Ac-Ala-Gln-Cys-Tyr-Lys-NH$_2$ (SEQ ID NO: 8); or

Ala-Gln-(N—CH$_3$)Cys-[(N—CH$_3$)]Tyr-Lys (SEQ ID NO: 9).

4. A compound of claim 1 wherein $A_1$ and $A_2$ both are a bond.

5. A compound of claim 4 which is:

Cys-Tyr-Lys;

Cys-Ala-Lys;

Cys-Ala-Lys-NH$_2$;

Ac-Cys-Tyr-Lys-NH$_2$;

(N—CH$_3$)Cys-[(N—CH$_3$)]Tyr-Lys; or

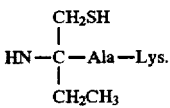

6. A compound of claim 1 wherein one of $A_1$ and $A_2$ is a bond.

7. A compound of claim 6 which is

Gln-Cys-Tyr-Lys (SEQ ID NO: 10);

Gln-Cys-Tyr-Lys-NH$_2$ (SEQ ID NO: 11);

Ala-Cys-Tyr-Lys (SEQ ID NO: 12);

Gln-Cys-Ala-Lys (SEQ ID NO: 13);

(N—CH$_3$)Ala-Cys-Tyr-Lys (SEQ ID NO: 14);

Gln-(N—CH$_3$)Cys-[(N—CH$_3$)]Tyr-Lys (SEQ ID NO: 15); and

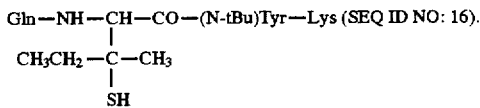

8. A formulation comprising a compound of claim 1 together with a pharmaceutically acceptable excipient, diluent, or carrier.

* * * * *